US006051554A

United States Patent [19]
Hornik et al.

[11] Patent Number: 6,051,554
[45] Date of Patent: *Apr. 18, 2000

[54] CONFORMATIONALLY CONSTRAINED BACKBONE CYCLIZED SOMATOSTATIN ANALOGS

[75] Inventors: Vered Hornik, Rehovot; Gary Gellerman, Rishon LeZion; Mich El M Afargan, Raanana, all of Israel

[73] Assignee: Peptor Limited, Rehovot, Israel

[ * ] Notice: This patent is subject to a terminal disclaimer.

[21] Appl. No.: 09/100,360

[22] Filed: Jun. 19, 1998

Related U.S. Application Data

[63] Continuation-in-part of application No. 08/690,609, Jul. 31, 1996, Pat. No. 5,748,643, and a continuation-in-part of application No. 08/488,159, Jun. 7, 1995, Pat. No. 5,811,392, and a continuation-in-part of application No. 08/569,042, Dec. 7, 1995.

[51] Int. Cl.$^7$ .......................... A61K 38/04; A61K 38/12; C07K 7/64
[52] U.S. Cl. .................. 514/11; 514/14; 514/15; 514/16; 514/17; 514/18; 530/311; 530/317; 530/327; 530/328; 530/329; 530/330
[58] Field of Search .................... 514/11, 14, 15, 514/16, 17, 18; 530/311, 317, 327, 328, 329, 330

[56] References Cited

U.S. PATENT DOCUMENTS

| 3,988,304 | 10/1976 | Garsky | 260/78 A |
|---|---|---|---|
| 4,011,182 | 3/1977 | Sarantakis | 260/8 |
| 4,054,558 | 10/1977 | Garsky | 260/112.5 S |
| 4,187,217 | 2/1980 | Chipens et al. | 260/112.5 R |
| 4,235,886 | 11/1980 | Freidinger et al. | 424/177 |
| 4,310,518 | 1/1982 | Freidinger et al. | 424/177 |
| 5,364,851 | 11/1994 | Joran | 530/345 |
| 5,371,070 | 12/1994 | Koerber et al. | 514/9 |
| 5,770,687 | 6/1998 | Hornik et al. | 530/311 |

FOREIGN PATENT DOCUMENTS

| 0 334 244 | 9/1989 | European Pat. Off. . |
|---|---|---|
| 0 336 779 | 10/1989 | European Pat. Off. . |
| 0 370 453 | 5/1990 | European Pat. Off. . |
| 0 395 417 | 10/1990 | European Pat. Off. . |
| 0 564 739 | 10/1993 | European Pat. Off. . |
| 2 304 352 | 10/1976 | France . |
| 2 411 828 | 7/1979 | France . |
| 41 19 544 | 10/1992 | Germany . |
| WO 89/01781 | 3/1989 | WIPO . |
| WO 92/00091 | 1/1992 | WIPO . |
| WO 92/22566 | 12/1992 | WIPO . |
| WO 93/01206 | 1/1993 | WIPO . |
| WO 94/11393 | 5/1994 | WIPO . |
| WO 95/01800 | 1/1995 | WIPO . |

OTHER PUBLICATIONS

Bell et al., 1993, "Molecular biology of somatostatin receptors", *TINS* 16:34–38.

Brazeau et al, 1973, "Hypothalamic Polypeptide That Inhibits the Secretion of Immunoreactive Pituitary Growth Hormone", *Science* 179:77–79.

Buscail et al., 1995, "Inhibition of cell proliferation by the somatostatin analogue RC–160 is mediated by somatostatin receptor subtypes SSTR2 and SSTR5 through different mechanisms", *Proc. Natl. Acad. Sci. USA* 92:1580–1584.

Byk et al., 1992, "Building Units for N–Backbone Cyclic Peptides. 1. Synthesis of Protected N–(ω–Aminoalkylene)amino Acids and Their Incorporation into Dipeptide Units", *J. Org. Chem.* 57:5687–5692.

Charpentier et al., 1989, "Synthesis and Binding Affinities of Cyclic and Related Linear Analogues of $CCK_8$ Selective for Central Receptors", *J. Med. Chem.* 32:1184–1190.

Giannis et al., 1993, "Peptidomimetics for Receptor Ligands—Discovery, Development, and Medical Perspectives", *Angew. Chem. Int. Ed. Engl.* 32:1244–1267.

Gilon et al., 1992, "SAR studies of cycloseptide: Effects of cyclization and charge at position 6", *Chem. Biol.* Proc Am Pept Symp 12th. pp. 476–477.

Gilon et al., 1991, "Backbone Cyclization: A New Method for Conferring Conformational Constraint on Peptides", *Biopolymers* 31:745–750.

Greiner et al., "Synthesis of New Backbone–Cyclized Bradykinin Analogs", Pept. 1994, Proc.Eur.Pept.Symp. 23rd Meeting Date 1994, 289–290.

Hruby et al., 1990, "Emerging approaches in the molecular design of receptor–selective peptide ligands: conformational, topographical and dynamic considerations", *Biochem. J.* 268:249–262.

Krstenansky et al., "Cyclic hexapeptide antagonists of the bradykinn $B_2$ receptor: Receptor binding and solution backbone conformation", *Letters in Peptide Science*, vol. 1 (1994) pp. 229–234.

Lamberts et al., 1990, "Somatostatin–Receptor Imaging in the Localization of Endocrine Tumors", *New England J. Med.* 323:1246–1249.

Lamberts, 1988, "The Role of Somatostatin in the Regulation of Anterior Pituitary Hormone Secretion and the Use of Its Analogs in the Treatment of Human Pituitary Tumors", *Endocrine Reviews* 9:417–436.

Lymangrover et al, 1983, "Varying the Duration of A23187 Administration Alters its Effect on Adrenal Steroidogenesis", *Life Sciences* 34:371–377.

Mosberg et al., 1983, "Bis–penicillamine enkephalins possess highly improved specificity toward Ōopioid receptors", *Proc. Natl. Acad. Sci. USA* 80:5871–5874.

(List continued on next page.)

*Primary Examiner*—Michael P. Woodward
*Assistant Examiner*—A. Gupta
*Attorney, Agent, or Firm*—Pennie & Edmonds LLP

[57] ABSTRACT

Novel peptides which are conformationally constrained backbone cyclized somatostatin analogs. Methods for synthesizing the somatostatin analogs and for producing libraries of the somatostatin analogs are also disclosed. Furthermore, pharmaceutical compositions comprising somatostatin analogs, and methods of using such compositions are disclosed.

15 Claims, 3 Drawing Sheets

OTHER PUBLICATIONS

Plotsky et al., 1985, "Patterns of Growth Hormone–Releasing Factor and Somatostatin Secretion into the Hypophysial–Portal Circulation of the Rat", *Science* 230:461–463.

Raynor et al., 1993, "Cloned Somatostatin Receptors: Identification of Subtype–Selective Peptides and Demonstration of High Affinity Binding of Linear Peptides", *Mol. Pharmacol.* 43:838–844.

Reisine et al., 1995, "Molecular Biology of Somatostatin Receptors", *Endocrine Reviews* 16:427–442.

Reubi et al., 1995, "Multiple actions of somatostatin in neoplastic disease", *TIPS* 16:110–115.

Rizo et al., 1992, "Constrained Peptides: Models of Bioactive Peptides and Protein Substructures", *Annu. Rev. Biochem.* 61:387–418.

Rodriguez et al., 1990, "Synthesis of cyclic analogues of cholecystokinin highly selective for central receptors", *Int. J. Peptide Protein Res.* 35:441–451.

Rudinger, 1976, "Characteristics of the Amino Acids as Components of a Peptide Hormone Sequence in Peptide Hormones" (ed. J.A. Parsons), University Park Press, Baltimore, pp. 1–7.

Steranka et al., 1988, "Bradykinin as a pain mediator: Receptors are localized to sensory neurons, and antagonists have analgesic actions", *Proc. Natl. Acad. Sci. USA* 85:3245–3249.

Veber et al., 1984, "A Super Active Cyclic Hexapeptide Analog of Somatostatin", *Life Sciences* 34:1371–1378.

Veber et al., 1985, "The design of metabolically–stable peptide analogs", *TINS* pp. 392–396.

Zuckerman, 1993, "The chemical synthesis of peptidomimetic libraries", *Current Opinion in Structural Biol.* 3:580–584.

CONFORMATIONALLY CONSTRAINED BACKBONE CYCLIZED SOMATOSTATIN ANALOGS

CROSS-REFERENCE TO RELATED APPLICATIONS

This application is a continuation-in-part of application Ser. No. 08/690,609 filed Jul. 31, 1996, now U.S. Pat. No. 5,748,643, and a continuation-in-part of application Ser. No. 08/488,159 filed Jun. 7, 1995, now. U.S. Pat. No. 5,811,392, and a continuation-in-part of application Ser. No. 08/569,042 filed Dec. 7, 1995.

FIELD OF THE INVENTION

The present invention relates to conformationally constrained $N^\alpha$ backbone-cyclized somatostatin analogs cyclized via novel linkages, and to pharmaceutical compositions containing same.

BACKGROUND OF THE INVENTION

Somatostatin analogs

Somatostatin is a cyclic tetradecapeptide found both in the central nervous system and in peripheral tissues. It was originally isolated from mammalian hypothalamus and identified as an important inhibitor of growth hormone secretion from the anterior pituitary. Its multiple biological activities include inhibition of the secretion of glucagon and insulin from the pancreas, regulation of most gut hormones and regulation of the release of other neurotransmitters involved in motor activity and cognitive processes throughout the central nervous system (for review see Lamberts, *Endocrine Rev.*, 9:427, 1988). Additionally, somatostatin and its analogs are potentially useful antiproliferative agents for the treatment of various types of tumors.

Natural somatostatin (also known as Somatotropin Release Inhibiting Factor, SRIF) of the following structure:

H-Ala$^1$-Gly$^2$-Cys$^3$-Lys$^4$-Asn$^5$-Phe$^6$-Phe$^7$-Trp$^8$-Lys$^9$-Thr$^{10}$-Phe$^{11}$-Thr$^{12}$-Ser$^{13}$-Cys$^{14}$-OH was first isolated by Guillemin and colleagues (Bruzeau et al. *Science*, 179:78, 1973). It exerts its effect by interacting with a family of receptors. Recently five receptor subtypes, termed SSTR1-5, have been identified and cloned. In its natural form, somatostatin has limited use as a therapeutic agent since it exhibits two undesirable properties: poor bioavailability and short duration of action. For this reason, great efforts have been made during the last two decades to find somatostatin analogs that will have superiority in either potency, biostability, duration of action or selectivity with regard to inhibition of the release of growth hormone, insulin or glucagon.

Structure-activity relation studies, spectroscopic techniques such as circular dichroism and nuclear magnetic resonance, and molecular modeling approaches reveal the following: the conformation of the cyclic part of natural somatostatin is most likely to be an antiparallel β-sheet; Phe$^6$ and Phe$^{11}$ play an important role in stabilizing the pharmacophore conformation through hydrophobic interactions between the two aromatic rings; the four amino acids Phe$^7$-Trp$^8$-Lys$^9$-Thr$^{10}$ which are spread around the β-turn in the antiparallel β-sheet are essential for the pharmacophore; and (D)Trp$^8$ is preferable to (L)Trp$^8$ for the interactions with somatostatin receptor subtypes 2 through 5.

Nevertheless, a hexapeptide somatostatin analog containing these four amino acids anchored by a disulfide bridge:

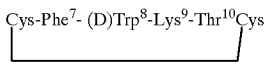

is almost inactive both in vitro and in vivo, although it has the advantage of the covalent disulfide bridge which replaces the Phe$^6$-Phe$^{11}$ hydrophobic interactions in natural somatostatin.

Four main approaches have been attempted in order to increase the activity of this hexapeptide somatostatin analog. (1) Replacing the disulfide bridge by a cyclization which encourages a cis-amide bond, or by performing a second cyclization to the molecule yielding a bicyclic analog. In both cases the resultant analog has a reduced number of conformational degrees of freedom. (2) Replacing the original residues in the sequence Phe$^7$-(D)Trp$^8$-Lys$^9$-Thr$^{10}$ with other natural or non-natural amino acids, such as replacing Phe$^7$ with Tyr$^7$ and Thr$^{10}$ with Val$^{10}$. (3) Incorporating additional functional groups from natural somatostatin with the intention that these new elements will contribute to the interaction with the receptor. (4) Eliminating one of the four amino acids Phe$^7$-(D)Trp$^8$-Lys$^9$-Thr$^{10}$ with the assumption that such analogs would be more selective.

The somatostatin analog, MK-678:

cyclo (N-Me-Ala$^6$-Tyr$^7$-(D)Trp$^8$-Lys$^9$-Val$^{10}$-Phe)

is an example of a highly potent somatostatin analog designed using the first three approaches above (Veber, et al., *Life Science*, 34:371, 1984). In this hexapeptide analog, a cis-amide bond is located between N-Me-Ala and Phe$^{11}$, Tyr$^7$ and Val$^{10}$ replace Phe$^7$ and Thr$^{10}$ respectively, and Phe$^{11}$ is incorporated from natural somatostatin.

Another group of somatostatin analogs (U.S. Pat. Nos. 4,310,518 and 4,235,886) includes Octreotide:

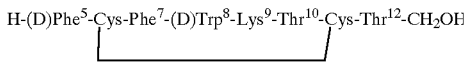

the only approved somatostatin analog currently available. It was developed using the third approach described above. Here, (D) Phe$^5$ and the reduced C-terminal Thr$^{12}$-CH$_2$OH are assumed to occupy some of the conformational space available to the natural Phe$^6$ and Thr$^{12}$, respectively.

The compound TT-232:

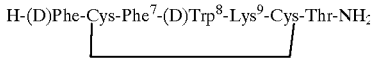

is closely related to Octreotide and is an example of implementing the fourth approach described above. The lack of Thr$^{10}$ is probably responsible for its high functional selectivity in terms of antitumor activity.

These examples of highly potent somatostatin analogs suggest that the phenylalanines in positions 6 and 11 not only play an important role in stabilizing the pharmacophore conformation but also have a functional role in the interaction with the receptor. It is still an open question whether one phenylalanine (either Phe$^6$ or Phe$^{11}$) is sufficient for the interaction with the receptor or whether both are needed.

It is now known that the somatostatin receptors constitute a family of five different receptor subtypes (Bell and Reisine, *Trends Neurosci.*, 16, 34–38, 1993), which may be distinguished on the basis of their tissue specificity and/or biological activity. Somatostatin analogs known in the art may not provide sufficient selectivity or receptor subtype selectivity, particularly as anti-neoplastic agents (Reubi and Laissue, *TIPS*, 16, 110–115, 1995).

Symptoms associated with metastatic carcinoid tumors (flushing and diarrhea) and vasoactive intestinal peptide (VIP) secreting adenomas (watery diarrhea) are treated with somatostatin analogs. Somatostatin has been also approved for the treatment of severe gastrointestinal hemorrhages. Somatostatin may also be useful in the palliative treatment of other hormone-secreting tumors (e.g., pancreatic islet-cell tumors and acromegaly) and hormone dependent tumors (e.g., chondrosarcoma and osteosarcoma) due to its anti-secretory activity.

Peptidomimetics

As a result of major advances in organic chemistry and in molecular biology, many bioactive peptides can now be prepared in quantities sufficient for pharmacological and clinical utilities. Thus in the last few years new methods have been established for the treatment and therapy of illnesses in which peptides have been implicated. However, the use of peptides as drugs is limited by the following factors: a) their low metabolic stability towards proteolysis in the gastrointestinal tract and in serum; b) their poor absorption after oral ingestion, in particular due to their relatively high molecular mass or the lack of specific transport systems or both; c) their rapid excretion through the liver and kidneys; and d) their undesired side effects in non-target organ systems, since peptide receptors can be widely distributed in an organism.

Moreover, with few exceptions, native peptides of small to medium size (less than 30 amino acids) exist unordered in dilute aqueous solution in a multitude of conformations in dynamic equilibrium which may lead to lack of receptor selectivity, metabolic susceptibilities and hamper attempts to determine the biologically active conformation. If a peptide has the biologically active conformation per se, i.e., receptor-bound conformation, then an increased affinity toward the receptor is expected, since the decrease in entropy on binding is less than that on the binding of a flexible peptide. It is therefore important to strive for and develop ordered, uniform and biologically active peptides.

In recent years, intensive efforts have been made to develop peptidomimetics or peptide analogs that display more favorable pharmacological properties than their prototype native peptides. The native peptide itself, the pharmacological properties of which have been optimized, generally serves as a lead for the development of these peptidomimetics. However, a major problem in the development of such agents lies in determining the active region of a biologically active peptide. For instance, frequently only a small number of amino acids (usually four to eight) are responsible for the recognition of a peptide ligand by a receptor. Once this biologically active site is determined a lead structure for development of peptidomimetic can be optimized, for example by structure-activity relationship studies.

As used herein, a "peptidomimetic" is a compound that, as a ligand of a receptor, can imitate (agonist) or block (antagonist) the biological effect of a peptide at the receptor level. The following factors should be considered to achieve the best possible agonist peptidomimetic a) metabolic stability, b) good bioavailability, c) high receptor affinity and receptor selectivity, and d) minimal side effects.

A generally applicable and successful method recently has been the development of conformationally restricted peptidomimetics that imitate the receptor-bound conformation of the endogenous peptide ligands as closely as possible (Rizo and Gierasch, *Ann. Rev. Biochem.*, 61:387, 1992). Investigations of these types of analogs show them to have increased resistance toward proteases, that is, an increase in metabolic stability, as well as increased selectivity and thereby fewer side effects (Veber and Friedinger, *Trends Neurosci.*, p. 392, 1985).

Once these peptidomimetic compounds with rigid conformations are produced, the most active structures are selected by studying the structure-activity relationships. Such conformational constraints can involve local modifications of structure or global conformational restraints (for review see Giannis and Kolter, *Angew. Chem. Int. Ed. Enql.* 32:1244, 1993).

Conformationally constrained Peptide analogs

Bridging between two neighboring amino acids in a peptide leads to a local conformational modification, the flexibility of which is limited in comparison with that of regular dipeptides. Some possibilities for forming such bridges include incorporation of lactams and piperazinones. γ-Lactams and δ-lactams have been designed to some extent as "turn mimetics"; in several cases the incorporation of such structures into peptides leads to biologically active compounds.

Global restrictions in the conformation of a peptide are possible by limiting the flexibility of the peptide strand through cyclization (Hruby et al., *Biochem. J.*, 268:249, 1990). Not only does cyclization of bioactive peptides improve their metabolic stability and receptor selectivity, cyclization also imposes constraints that enhance conformational homogeneity and facilitates conformational analysis. The common modes of cyclization are the same found in naturally occurring cyclic peptides. These include side chain to side chain cyclization or side chain to end-group cyclization. For this purpose, amino acid side chains that are not involved in receptor recognition are connected together or to the peptide backbone. Another common cyclization is the end-to-end cyclization.

The main limitations to these classical modes of cyclization are that they require substitution of amino acid side chains in order to achieve cyclization.

Another conceptual approach to the conformational constraint of peptides was introduced by Gilon, et al., (*Biopolymers* 31:745, 1991) who proposed backbone to backbone cyclization of peptides. The theoretical advantages of this strategy include the ability to effect cyclization via the carbons or nitrogens of the peptide backbone without interfering with side chains that may be crucial for interaction with the specific receptor of a given peptide. While the concept was envisaged as being applicable to any linear peptide of interest, in point of fact the limiting factor in the proposed scheme was the availability of suitable building units that must be used to replace the amino acids that are to be linked via bridging groups. The actual reduction to practice of this concept of backbone cyclization was prevented by the inability to devise any practical method of preparing building units of amino acids other than glycine (Gilon et al., *J. Org. Chem*, 587:5687, 1992). When syntheses of analogs of other amino acids were attempted the method used was unsuccessful or of such low yield as to preclude any general applicability.

In Gilon, EPO Application No. 564,739 A2; and *J. Org. Chem.*, 57:5687, 1992, two basic approaches to the synthesis of building units are described. The first starts with the reaction of a diamine with a bromo acid. Selective protection of the ω amine and further elaboration of protecting groups provides a building unit, suitable for Boc chemistry peptide synthesis. The second approach starts with selective protection of a diamine and reaction of the product with chloroacetic acid to provide the protected glycine derivative, suitable for Fmoc peptide synthesis.

Both examples deal with the reaction of a molecule of the general type X-CH(R)-CO-OR' (wherein X represents a leaving group which, in the examples given, is either Br or Cl) with an amine which replaces the X. The amine bears an alkylidene chain which is terminated by another functional group, amine in the examples described, which may or may not be blocked by a protecting group.

In all cases the a nitrogen of the end product originates in the molecule which becomes the bridging chain for subsequent cyclization. This approach was chosen in order to take advantage of the higher susceptibility to nucleophilic displacement of a leaving group next to a carboxylic group.

In a molecule where R is different than hydrogen there is a high tendency to eliminate HX under basic conditions. This side reaction reduces the yield of Gilon's disclosed method to the point where it is impractical for production of building units based on amino acids other than glycine. The diamine nitrogen is primary while the product contains a secondary nitrogen, which is a better nucleophile. So while the desired reaction is generally sluggish, and requires the addition of catalysts, the product is commonly contaminated with double alkylation products. There is no mention of building units with end group chemistries other than nitrogen, so the only cyclization schemes possible are backbone to side chain and backbone to C terminus.

Libraries of backbone cyclized peptide analogs

As mentioned above linear peptides suffer from several serious drawbacks as potential drugs, inasmuch as they are notoriously unstable in vivo, often lack high affinity of binding to their receptor, frequently lack selectively to one kind of receptor, and generally have poor oral bioavailability. In efforts to overcome such problems, it is also possible to utilize the methodologies developed in connection with synthetic peptide libraries to generate collections of cyclic peptides, novel biopolymers and even novel branched oligomeric compounds (reviewed by Zuckermann, Current Opinion in Structural Biology 3, 580–584, 1993).

The generation of libraries of cyclic peptides requires that in addition to any previously stated considerations, the cyclization reaction be performed in a high yield and with a minimum of additional manipulations. Unfortunately, classical cyclization reactions are highly sequence dependent in terms of the expected yields, making the uniform cyclization of a peptide mixture unreliable.

Recent advances in the cyclization of peptides directly on the solid support have improved the synthetic procedure, and even allowed the automation of cyclization reactions based on known cyclization schemes. In the past, cyclizations were typically performed in solution under conditions of high dilution. Polymer-supported cyclizations can both avoid potential side reactions such as oligomerization and facilitate product purification. For example, on-resin cyclization methods have recently been used to prepare cyclopeptides with bridges formed of thioethers, disulfides, or lactams between two side chains, lactam between the amino terminus and a side chain, and lactams between the amino and carboxy termini (reviewed by Zuckermann, Current Opinion in Structural Biology 3, ibid).

The use of resin-bound cyclic peptides and free cyclic peptides in combinatorial libraries is disclosed in WO 92/00091. These cyclic peptides do not contain any conformationally constraining element, however, and in cases where cyclization is achieved, these peptides may still adopt a number of conformations and suffer many of the same shortcomings as linear peptides.

Cyclic semi-random peptide libraries, disclosed in WO 95/01800, are exclusively cyclic penta- and hexa-peptide libraries containing one or more randomized amino acids and a conformationally constraining element in the form of an amino acid residue such as proline which fixes the beta turn angles of the adjacent amino acid residues. The advantages of such conformationally constraining elements is stressed by the inventors of this approach. However, inclusion of such elements via incorporation of a particular amino acid residue into the peptide sequence may have detrimental effects on those residues required for receptor recognition or other biological activity. Furthermore, in that application, the cyclization reaction is merely another coupling reaction in which the terminal amino group of the linear peptide is coupled to the terminal carboxy group of the peptide.

SUMMARY OF THE INVENTION

According to the present invention, novel peptidomimetic compounds, which are characterized in that they incorporate novel building units with bridging groups attached to the alpha nitrogens of alpha amino acids, have now been generated. Specifically, these compounds are backbone cyclized somatostatin analogs comprising a peptide sequence of four to twelve amino acids that incorporates at least two building units, each of which contains one nitrogen atom of the peptide backbone connected to a bridging group comprising an amide, thioether, thioester or disulfide, wherein the at least two building units are connected to the bridging group to form a cyclic structure. Preferably, the peptide sequence incorporates five to eight amino acids.

For the most preferred analogs, the amino acid Asn was substituted by the backbone Phe building unit at position 5. The configuration substitution of the native L-Trp at position 8 to D-Trp was made to improve the stability of the analog. The Thr residue at position 10 was substituted by the corresponding backbone Phe building unit. The unique configuration substitution at position 9 from L-Lys to D-Lys as shown in PTRs 3123 and 3171 in comparison to PTR 3113 imparts improved selectivity of binding to the SST receptor subtype SSTR3 rather than SSTR5.

The backbone cyclized somatostatin analogs of the invention preferably have the general formula

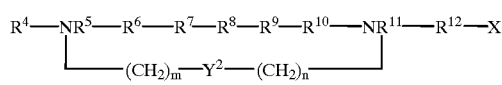

wherein m and n are 1 to 5 an preferably 1, 2 or 3;

X designates a terminal carboxy acid, amide or alcohol group;

$R^4$ is absent or is a terminal group of one to four amino acids;

$R^5$ is Nal, β-Asp (Ind), Gly, Tyr, (D)- or (L)-Ala, or (D)- or (L)-Phe;

$R^6$ and $R^7$ may be absent, or are independently Gly, Tyr, (D)- or (L)-Ala, or (D)- or (L)-Phe;

$R^8$ is (D)- or (L)-Trp;

$R^9$ is (D)- or (L)-Lys;

$R^{10}$ is absent or is Gly, Abu, Cys, Thr, Val, (D)- or (L)-Ala, or (D)- or (L)-Phe;

$R^{11}$ is Cys, (D)- or (L)-Ala, or (D)- or (L)-Phe;

$R^{12}$ is absent or is Val, Thr, or Nal; and $Y^2$ is amide, thioether, thioester or disulfide.

The most preferred backbone cyclized somatostatin analogs of the invention are:

NPhe - Phe - D-Trp - Lys - Thr - NPhe - X
NPhe - D-Trp - Lys - Thr - NPhe - X
NPhe - D-Trp - D-Lys - Thr - NPhe - X
NAla - D-Trp - Lys - Ala - NPhe - X
NAla - D-Trp - Lys - Thr - NPhe - X
NAla - D-Trp - Lys - Thr - NAla - X
NAla - Phe - D-Trp - Lys - Thr - NAla - X
NAla - Tyr - D-Trp - Lys - Val - NPhe - X
NAla - Phe - D-Trp - D-Lys - Thr - NAla - X
ND-Phe - Ala - Phe - D-Trp - Lys - NAla - X
NAla - D-Trp - Lys - Thr - NAla - X
NAla - D-Trp - Lys - Thr - NCys - X
NAla - D-Trp - Lys - Thr - Cys - NThr - X
NAla - Phe - D-Trp - NLys - Cys - X
NAla - Phe - D-Trp - Lys - Thr - Cys - NThr - X
NPhe - Phe - Phe - D-Trp - Lys - NPhe - X
NPhe - Phe - Phe - D-Trp - D-Lys - NPhe - X or
Phe* - Phe - Phe - D-Trp - D-Lys - NPhe - X where X is -NH$_2$ or -OH and the bridging group extends between the amino acids preceded with an N. For the last peptide, the asterisk designates that the bridging group is connected between the backbone and the N terminus.

These backbone cyclized somatostatin peptide analogs are prepared by incorporating at least one N$^\alpha$-ω-functionalized derivative of an amino acids into a peptide sequence and subsequently selectively cyclizing the functional group with one of the side chains of the amino acids in the peptide sequence or with another ω-functionalized amino acid derivative. The N$^\alpha$-ω-functionalized derivative of amino acids preferably have the following formula:

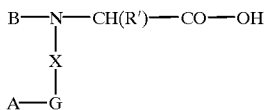

wherein X is a spacer group selected from the group consisting of alkylene, substituted alkylene, arylene, cycloalkylene and substituted cycloalkylene; R' is an amino acid side chain, optionally bound with a specific protecting group; B is a protecting group selected from the group consisting of alkyloxy, substituted alkyloxy, or aryl carbonyls; and G is a functional group selected from the group consisting of amines, thiols, alcohols, carboxylic acids and esters, aldehydes, alcohols and alkyl halides; and A is a specific protecting group of G.

Preferred building units are the co-functionalized amino acid derivatives wherein X is alkylene; G is a thiol group, an amine group or a carboxyl group; R' is phenyl, methyl or isobutyl; with the proviso that when G is an amine group, R' is other than H. Further preferred are ω-functionalized amino acid derivatives wherein R' is protected with a specific protecting group.

More preferred are ω-functionalized amino acid derivatives wherein G is an amino group, a carboxyl group, or a thiol group of the following formulae:

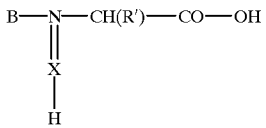

-continued

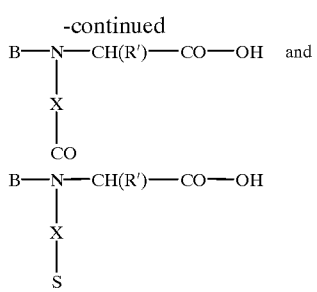

wherein X, R' and B are as defined above.

The most striking advantages of these methods are:

1) cyclization of the peptide sequence is achieved without compromising any of the side chains of the peptide thereby decreasing the chances of sacrificing functional groups essential for biological recognition and function.

2) optimization of the peptide conformation is achieved by allowing permutation of the bridge length, direction, and bond type (e.g., amide, disulfide, thioether, thioester, etc.) and position of the bond in the ring.

3) when applied to cyclization of linear peptides of known activity, the bridge can be designed in such a way as to minimize interaction with the active region of the peptide and its cognate receptor. This decreases the chances of the cyclization arm interfering with recognition and function, and also creates a site suitable for attachment of tags such as radioactive tracers, cytotoxic drugs, light capturing substances, or any other desired label.

Backbone cyclized analogs of the present invention may be used as pharmaceutical compositions and in methods for the treatment of disorders including: post-surgical pain, all types of inflammation, in particular pancreatitis, cancers, endocrine disorders and gastrointestinal disorders. The pharmaceutical compositions comprising pharmacologically active backbone cyclized peptide agonists or antagonists and a pharmaceutically acceptable carrier or diluent represent another embodiment of the invention, as do the methods for the treatment of inflammation, cancer or endocrine disorders and gastrointestinal disorders using such compositions.

To efficiently determine which peptide analogs are the lost useful for a particular treatment, a library of the analogs can be prepared. These libraries enable varying conformation as well as level of flexibility (constraint) in order to find the optimal backbone conformation of the peptide in performing its role as an agonist or antagonist. This is accomplished by varying both the position of the bridgeheads (i.e., the positions in the linear sequence of residues that are to be cyclized), as well as varying the length, the direction and the bond type of the bridge between these units. The preparation of these libraries as well as the resulting libraries form yet another embodiment of the invention.

DETAILED DESCRIPTION OF THE INVENTION

Figure 1:
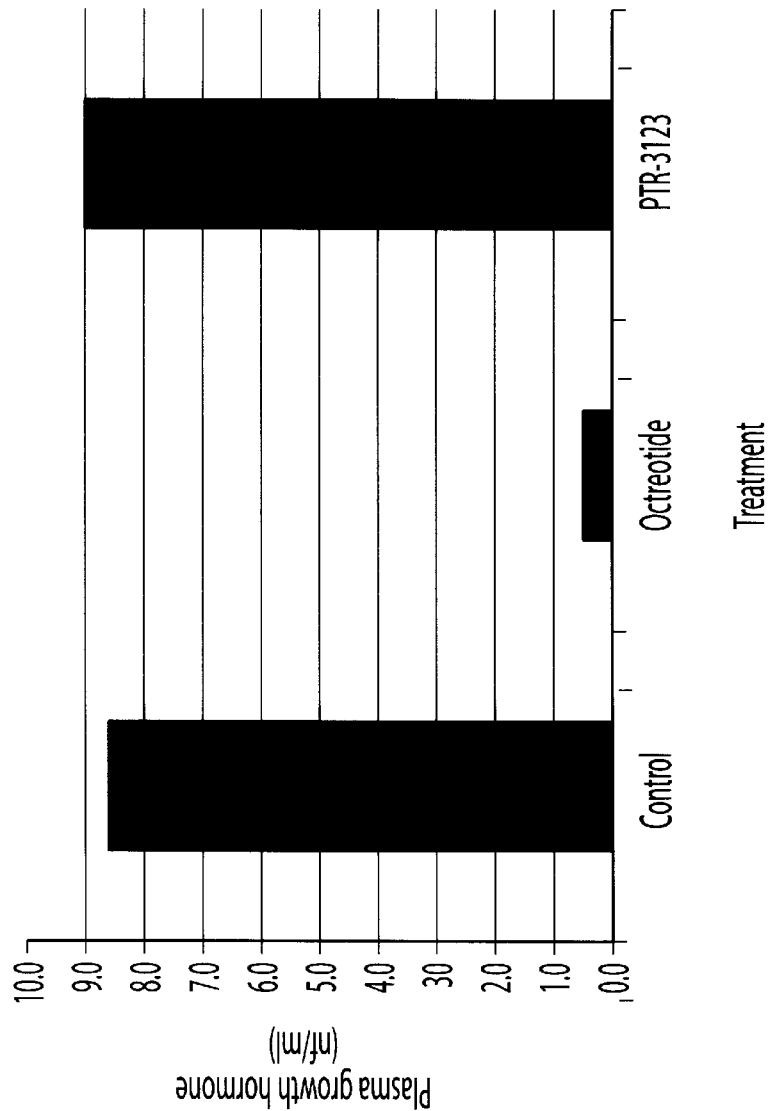
FIG. 1 is a graph showing the effect of somatostatin analogs on the release of growth hormone compared to octreotide.

The compounds herein described may have asymmetric centers. All chiral, diastereomeric, and racemic forms are included in the present invention. Many geometric isomers of olefins and the like can also be present in the compounds described herein, and all such stable isomers are contemplated in the present invention.

By "stable compound" or "stable structure" is meant herein a compound that is sufficiently robust to survive isolation to a useful degree of purity from a reaction mixture, and formulation into an efficacious therapeutic agent.

As used herein and in the claims, "alkyl" or "alkylenyl" is intended to include both branched and straight-chain saturated aliphatic hydrocarbon groups having one to ten carbon atoms; "alkenyl" is intended to include hydrocarbon chains of either a straight or branched configuration having two to ten carbon atoms and one or more unsaturated carbon-carbon bonds which may occur in any stable point along the chain, such as ethenyl, propenyl, and the like; and "alkynyl" is intended to include hydrocarbon chains of either a straight or branched configuration having from two to ten carbon atoms and one or more triple carbon-carbon bonds which may occur in any stable point along the chain, such as ethynyl, propynyl, and the like.

As used herein and in the claims, "aryl" is intended to mean any stable 5- to 7-membered monocyclic or bicyclic or 7- to 14-membered bicyclic or tricyclic carbon ring, any of which may be saturated, partially unsaturated or aromatic, for example, phenyl, naphthyl, indanyl, or tetrahydronaphthyl tetralin, etc.

As used herein and in the claims, "alkyl halide" is intended to include both branched and straight-chain saturated aliphatic hydrocarbon groups having the one to ten carbon atoms, wherein 1 to 3 hydrogen atoms have been replaced by a halogen atom such as Cl, F, Br, and I.

As used herein and in the claims, the phrase "therapeutically effective amount" means that amount of novel backbone cyclized peptide analog or composition comprising same to administer to a host to achieve the desired results for the indications described herein, such as but not limited of inflammation, cancer, endocrine disorders and gastrointestinal disorders.

The term, "substituted" as used herein and in the claims, means that any one or more hydrogen atoms on the designated atom is replaced with a selection from the indicated group, provided that the designated atom's normal valency is not exceeded, and that the substitution results in a stable compound.

When any variable (for example R, X, Z, etc.) occurs more than one time in any constituent or in any Formula herein, its definition on each occurrence is independent of its definition at every other occurrence. Also, combinations of substituents and/or variables are permissible only if such combinations result in stable compounds.

As used herein "peptide" indicates a sequence of amino acids linked by peptide bonds. The somatostatin peptide analogs of this invention comprise a sequence of amino acids of 4 to 24 amino acid residues, preferably 6 to 14 residues, each residue being characterized by having an amino and a carboxy terminus.

A "building unit" indicates an N$^\alpha$ derivatized α amino acid of the general Formula IV:

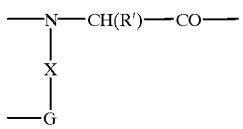

Formula (IV)

wherein X is a spacer group selected from the group consisting of alkylene, substituted alkylene, arylene, cycloalkylene and substituted cycloalkylene; R' is an amino acid side chain, optionally bound with a specific protecting group; and G is a functional group selected from the group consisting of amines, thiols, alcohols, carboxylic acids and esters, and alkyl halides; which is incorporated into the peptide sequence and subsequently selectively cyclized via the functional group G with one of the side chains of the amino acids in said peptide sequence or with another ω-functionalized amino acid derivative.

The methodology for producing the building units is described in international patent applications PCT/IB95/00455 and PCT/IL97/00261, both of which are expressly incorporated herein by reference thereto for further details of this methodology. The building units are abbreviated by the three letter code of the corresponding modified amino acid followed by the type of reactive group (N for amine, C for carboxyl), and an indication of the number of spacing methylene groups. For example, Gly-C2 describes a modified Gly residue with a carboxyl reactive group and a two carbon methylene spacer, and Phe-N3 designates a modified phenylalanine group with an amino reactive group and a three carbon methylene spacer.

As used herein "linear peptide" denotes the peptide sequence that is constructed only of amino acid residues and is devoid of any building units.

As used herein "backbone cyclic peptide" denotes an analog of a linear peptide which contains at least one building unit that has been liked to form a bridge via the alpha nitrogen of the peptide backbone to another building unit, or to another amino acid in the sequence.

As used herein "pre-cyclic peptide" denotes an analog identical to the cyclic analog except that it is retained in the non-cyclized form to serve as control during the biological or other screening assays. The term non-cyclic can be used interchangeably with the term pre-cyclic.

Certain abbreviations are used herein to describe this invention and the manner of making and using it. For instance, AcOH refers to acetic acid, Ada refers to adamantanacetyl, Adac refers to adamantanecarbonyl, Alloc refer to allyloxycarbonyl, Boc refers to the t-butyloxycarbonyl radical, BOP refers to benzotriazol-1-yloxy-tris-(dimethylamino)phosphonium hexafluorophosphate, BSA refers to bovine serum albumin, Cbz refers to the carbobenzyloxy radical, DCC refers to dicyclohexylcarbodiimide, DCM refers to Dichloromethane, Dde refers to 1-(4,4-dimethyl2,6-dioxocyclohex-1-ylidene-ethyl), DIEA refers to diisopropyl-ethyl amine, DMF refers to dimethyl formamide, DPPA refers to diphenylphosphoryl azide, Dtc refers to 5,5-dimethylthiazolidine-4-carboxylic acid, EDC refers to N-ethyl-N' (dimethylaminopropyl)-carbodiimide, EDT refers to ethanedithiol, Fmoc refers to the fluorenylmethoxycarbonyl radical, GPI refers to guinea pig ileum, HATU refers to [O-(7-azabenzotriazol-1-yl)-1,1,3,3-tetramethyl uronium hexafluorophosphate, HBTU refers to 1-hydroxybenztriazolyltetramethyl-uronium hexafluorophosphate, HF refers to hydrofluoric acid, HOBT refers to 1-hydroxybenzotriazole, HPLC refers to high pressure liquid chromatography, MALDI-TOF MS refers to matrix-assisted laser desorption, time-of-flight mass spectrometry, Mts refers to the 4-methoxy-2,3,6-trimethylbenzenzsulfonyl, NBT refers to nitro blue tetrazolium, NMM refers to N-methylmorpholine, NMP refers to 1-methyl-2-pyrolidonone, PBS refers to phosphate buffered saline, Pmc refers to pentamethylchroman-6-sulfonyl, PNPP refers to p-nitrophenyl phosphate, PPA refers to 1-propanephosphoric acid cyclic anhydride, PyBOP refers to Benzotriazole-1-yl-oxy-tris-pyrrolidino-phosphonium hexafluorophosphate, PyBrOP refers to Bromo-tris-pyrrolidino-phosphonium hexafluorophosphate, RT refers to room temperature, SMPS refers to simultaneous multiple peptide synthesis, SRIF refers to Somatotropin Release Inhibitory Factor, TBTU refers to 2-(1H-benzotriazole-1-yl)-1,1,3,3-tetramethyluronium tetrafluoroborate, t-Bu refers to the tertiary butyl radical, TFA refers to trifluoroacetic acid, TIS refers to triisopropylsilane, Tpr refers to thiazolidine-4-carboxylic acid, Trt refers to trityl, Ts refers to toluenesulfonyl.

The amino acids used in this invention are those which are available commercially or are available by routine synthetic methods. Certain residues may require special methods for incorporation into the peptide, and either sequential, divergent and convergent synthetic approaches to the peptide sequence are useful in this invention. Natural coded amino acids and their derivatives are represented by three-letter codes according to IUPAC conventions. When there is no indication, the L isomer was used. The D isomers are indicated by "D" before the residue abbreviation. List of Non-coded amino acids: Abu refers to 2-aminobutyric acid, Aib refers to 2-amino-isobutyric acid, Cha refers to cyclohexylalanine, Hcys refer to homocystein, Hyp refers to S-trans-4-hydroxyproline, 1Nal refers to 1-naphthylalanine, 2Nal refers to 2-naphtylalanine, Nva refers to norvaline, Oic refers to octahydroindolecarboxylic acid, Phg refers to phenylglycine, pClPhe refers to p-chloro-phenylalanine, pFPhe refers to p-fluoro-phenylalanine, pNO$_2$Phe refers to p-nitro-phenylalanine, Thi refers to thienylalanine.

Synthetic Approaches

According to the present invention peptide analogs are cyclized via bridging groups attached to the alpha nitrogens of amino acids that permit novel non-peptidic linkages. In general, the procedures utilized to construct such peptide analogs from their building units rely on the known principles of peptide synthesis; most conveniently, the procedures can be performed according to the known principles of solid phase peptide synthesis. The innovation requires replacement of one or more of the amino acids in a peptide sequence by novel building units of the general Formula:

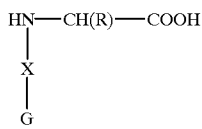

wherein R is the side chain of an amino acid, X is a spacer group and G is the functional end group by means of which cyclization will be effected. The side chain R is the side chain of any natural or synthetic amino acid that is selected to be incorporated into the peptide sequence of choice. X is a spacer group that is selected to provide a greater or lesser degree of flexibility in order to achieve the appropriate conformational constraints of the peptide analog. Such spacer groups include alkylene chains, substituted, branched and unsaturated alkylenes, arylenes, cycloalkylenes, and unsaturated and substituted cycloalkylenes. Furthermore, X and R can be combined to form a heterocyclic structure.

The terminal (ω) functional groups to be used for cyclization of the peptide analog include but are not limited to:

a. Amines, for reaction with electrophiles such as activated carboxyl groups, aldehydes and ketones (with or without subsequent reduction), and alkyl or substituted alkyl halides.

b. Alcohols, for reaction with electrophiles such as activated carboxyl groups.

c. Thiols, for the formation of disulfide bonds and reaction with electrophiles such as activated carboxyl groups, and alkyl or substituted alkyl halides.

d. 1,2 and 1,3 Diols, for the formation of acetals and ketals.

e. Alkynes or Substituted Alkynes, for reaction with nucleophiles such as amines, thiols or carbanions; free radicals; electrophiles such as aldehydes and ketones, and alkyl or substituted alkyl halides; or organometallic complexes.

f. Carboxylic Acids and Esters, for reaction with nucleophiles (with or without prior activation), such as amines, alcohols, and thiols.

g. Alkyl or Substituted Alkyl Halides or Esters, for reaction with nucleophiles such as amines, alcohols, thiols, and carbanions (from active methylene groups such as acetoacetates or malonates); and formation of free radicals for subsequent reaction with alkenes or substituted alkenes, and alkynes or substituted alkynes.

h. Alkyl or Aryl Aldehydes and Ketones for reaction with nucleophiles such as amines (with or without subsequent reduction), carbanions (from active methylene groups such as acetoacetates or malonates), diols (for the formation of acetals and ketals).

i. Alkenes or Substituted Alkenes, for reaction with nucleophiles such as amines, thiols, carbanions, free radicals, or organometallic complexes.

j. Active Methylene Groups, such as malonate esters, acetoacetate esters, and others for reaction with electrophiles such as aldehydes and ketones, alkyl or substituted alkyl halides.

It will be appreciated that during synthesis of the peptide these reactive end groups, as well as any reactive side chains, must be protected by suitable protecting groups.

Suitable protecting groups for amines are alkyloxy, substituted alkyloxy, and aryloxy carbonyls including, but not limited to, tert butyloxycarbonyl (Boc), Fluorenylmethyloxycarbonyl (Fmoc), Allyloxycarbonyl (Alloc) and Benzyloxycarbonyl (Z).

Carboxylic end groups for cyclizations may be protected as their alkyl or substituted alkyl esters or thio esters or aryl or substituted aryl esters or thio esters. Examples include but are not limited to tertiary butyl ester, allyl ester, benzyl ester, 2-(trimethylsilyl)ethyl ester and 9-methyl fluorenyl.

Thiol groups for cyclizations may be protected as their alkyl or substituted alkyl thio ethers or disulfides or aryl or substituted aryl thio ethers or disulfides. Examples of such groups include but are not limited to tertiary butyl, trityl (triphenylmethyl), benzyl, 2-(trimethylsilyl)ethyl, pixyl(9-phenylxanthen-9-yl), acetamidomethyl, carboxymethyl, 2-thio-4-nitropyridyl.

It will further be appreciated by the artisan that the various reactive moieties will be protected by different protecting groups to allow their selective removal. Thus, a particular amino acid will be coupled to its neighbor in the peptide sequence when the N$^\alpha$ is protected by, for instance, protecting group A. If an amine is to be used as an end group for cyclization in the reaction scheme the $N^\omega$ will be protected by protecting group B, or an e amino group of any lysine in the sequence will be protected by protecting group C, and so on.

The coupling of the amino acids to one another is performed as a series of reactions as is known in the art of peptide synthesis. Novel building units of the invention, namely the $N^\alpha$-ω functionalized amino acid derivatives are incorporated into the peptide sequence to replace one or more of the amino acids. If only one such $N^\alpha$-ω functionalized amino acid derivative is selected, it will be cyclized to a side chain of another amino acid in the sequence. For instance: (a) an $N^\alpha$-(ω-amino alkylene) amino acid can be linked to the carboxyl group of an aspartic or glutamic acid residue; (b) an $N^\alpha$-(ω-carboxylic alkylene) amino acid can be linked to the ε- amino group of a lysine residue; (c) an $N^\alpha$-(ω-thio alkylene) amino acid can be linked to the thiol group of a cysteine residue; and so on. A more preferred embodiment of the invention incorporates two such $N^\alpha$-ω-functionalized amino acid derivatives which may be linked to one another to form N-backbone to N-backbone cyclic peptide analogs. Three or more such building units can be incorporated into a peptide sequence to create bi-cyclic peptide analogs as will be elaborated below. Thus, peptide analogs can be constructed with two or more cyclizations, including N-backbone to N-backbone, as well as backbone to side-chain or any other peptide cyclization.

As stated above, the procedures utilized to construct somatostatin analogs of the present invention from novel building units generally rely on the known principles of peptide synthesis. However, it will be appreciated that accommodation of the procedures to the bulkier building units of the present invention may be required. Coupling of the amino acids in solid phase peptide chemistry can be achieved by means of a coupling agent such as but not limited to dicyclohexycarbodiimide (DCC), bis(2-oxo-3-oxazolidinyl) phosphinic chloride (BOP-Cl), benzotriazolyl-N-oxytrisdimethyl-aminophosphonium hexafluoro phosphate (BOP), 1-oxo-1-chlorophospholane (Cpt-Cl), hydroxybenzotriazole (HOBT), or mixtures thereof.

It has now been found that coupling of the subsequent amino acid to the bulky building units of the present invention may require the use of additional coupling reagents including, but not limited to: coupling reagents such as PYBOP® (Benzotriazole-1-yl-oxy-tris-pyrrolidino-phosphonium hexafluorophosphate), PyBrOP® (Bromo-tris-pyrrolidino-phosphonium hexafluorophosphate), HBTU (2-(1H-Benzotriazole-1-yl)-1,1,3,3-tetramethyluronium hexafluoro-phosphate), TBTU (2-(1H-Benzotriazole-1-yl)-1,1,3,3-tetramethyluronium tetrafluoroborate).

Novel coupling chemistries may be used, such as pre-formed urethane-protected N-carboxy anhydrides (UNCA'S) and pre-formed acyl halides most preferably acyl chlorides. Such coupling may take place at room temperature and also at elevated temperatures, in solvents such as toluene, DCM (dichloromethane), DMF (dimethylformamide), DMA (dimethylacetamide), NMP (N-methyl pyrrolidinone) or mixtures of the above.

The preferred backbone cyclized somatostatin analogs of the present invention are now described. One embodiment has the following formula:

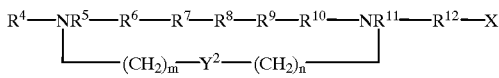

wherein m and n are 1 to 5;
X designates a terminal carboxy acid, amide or alcohol group;
$R^4$ is absent or is a terminal group of one to four amino acids;
$R^5$ is Nal, β-Asp (Ind), Gly, Tyr, (D)- or (L)-Ala, or (D)- or (L)-Phe;
$R^6$ and $R^7$ may be absent, or are independently Gly, Tyr, (D)- or (L)-Ala, or (D)- or (L)-Phe;
$R^7$ is (D)- or (L)-Trp;
$R^9$ is (D)- or (L)-Lys;
$R^{10}$ is absent or is Gly, Abu, Cys, Thr, Val, (D)- or (L)-Ala, or (D)- or (L)-Phe;
$R^{11}$ is Cys, (D)- or (L)-Ala, or (D)- or (L)-Phe;
$R^{12}$ is absent or is Val, Thr, or Nal; and
$Y^2$ is amide, thioether, thioester or disulfide.
Preferably:
$R^4$ is absent;
$R^5$ is (D)- or (L)-Phe, or (D)- or (L)-Ala;
$R^6$ may be absent and $R^6$, when present, and $R^7$ are independently (D)- or (L)-Phe, Ala or Tyr;
$R^{10}$ is absent or is Thr, Val or (D)- or (L)-Phe;
$R^{11}$ is (D)- or (L)-Ala, or (D)- or (L)-Phe; and
$R^{12}$ is absent.
Alternatively:
$R^5$ is (D)- or (L)-Ala, or (D)- or (L)-Phe;
$R^6$ is absent or is (D)- or (L)-Ala, or (D)- or (L)-Phe;
$R^7$ is (D)- or (L)-Ala, or (D)- or (L)-Phe;
$R^{10}$ is absent or is Thr, Cys, (D)- or (L)- Ala;
$R^{11}$ is Cys, (D)- or (L)-Ala, or (D)- or (L)-Phe; and
$R^{12}$ is absent or is Thr.
Another embodiment has the general formula:

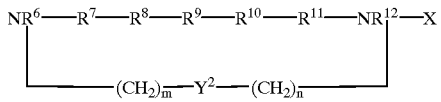

wherein: m and n are 1 to 5
$R^6$ is (D)- or (L)-Ala, or (D)- or (L)-Phe;
$R^7$ is absent or is Tyr, (D)- or (L)- Ala, or (D)- or (L)- Phe;
$R^{10}$ is Thr, Val, Cys or (D)- or (L)-Ala;
$R^{11}$ is Cys, (D)- or (L)-Ala, or (D) or (L)-Phe;
$R^{12}$ is Thr; and
$Y^2$ is amide, thioether, thioester or disulfide. Preferably:
$R^6$ is (D)- or (L)-Ala;
$R^7$ is absent or is (D)- or (L)-Phe;
$R^{10}$ is Thr;
$R^{11}$ is Cys; and
X is an alcohol group.
Yet another embodiment has the general formula:

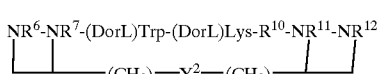

wherein: the dotted line indicates that the bridge is connected to $NR^6$ or $NR^7$ at one end and to $NR^{11}$ or $NR^{12}$ at the other end;

$R^6$ is absent or is (D)- or (L)-Phe or Ala;

$R^7$ is (D)- or (L)-Phe, Ala or Tyr;

$R^8$ is Thr, Ala, Val or Cys;

$R^{11}$ is absent or is (D)- or (L)-Phe, Ala or Cys;

$R^{12}$ is absent or is Thr or Thr reduced to an alcohol; and $Y^2$ is amide, thioether, thioester or amide. Preferably, the bridge is connected to $NR^6$ and $NR^{11}$ or to $NR^6$ and $NR^{12}$ with $R^{12}$ being Thr reduced to an alcohol.

The most preferred backbone cyclized somatostatin analogs of the invention are:

NPhe - Phe - D-Trp - Lys - Thr - NPhe - X
NPhe - D-Trp - Lys - Thr - NPhe - X
NPhe - D-Trp - D-Lys - Thr - NPhe - X
NAla - D-Trp - Lys - Ala - NPhe - X
NAla - D-Trp - Lys - Thr - NPhe - X
NAla - D-Trp - Lys - Thr - NAla - X
NAla - Phe - D-Trp - Lys - Thr - NAla - X
NAla - Tyr - D-Trp - Lys - Val - NPhe - X
NAla - Phe - D-Trp - D-Lys - Thr - NAla - X
ND-Phe - Ala - Phe - D-Trp - Lys - NAla - X
NAla - D-Trp - Lys - Thr - NAla - X
NAla - D-Trp - Lys - Thr - NCys - X
NAla - D-Trp - Lys - Thr - Cys - NThr - X
NAla - Phe - D-Trp - NLys - Cys - X
NAla - Phe - D-Trp - Lys - Thr - Cys - NThr - X
NPhe - Phe - Phe - D-Trp - Lys - NPhe - X
NPhe - Phe - Phe - D-Trp - D-Lys - NPhe - X or
Phe* - Phe - Phe - D-Trp - D-Lys - NPhe - X where X is -NH$_2$ or -OH and the bridging group extends between the amino acids preceded with an N. The asterisk designates where the bridging group is attached. For the last peptide mentioned above, the bridge is connected between the backbone and the N terminus.

Somatostatin is a tetradecapeptide hormone whose numerous regulatory functions are mediated by a family of five receptors, whose expression is tissue dependent. Receptor specific analogs of somatostatin are believed to be valuable therapeutic agents in the treatment of various diseases. Attempts to design small peptide analogs having this selectivity have not been highly successful. It has now unexpectedly been found that the conformationally constrained backbone cyclized somatostatin analogs of the present invention, and the hexapeptide analogs in particular, are highly selective to SST receptor subtypes.

The backbone cyclic-peptide designated PTR 3123, PTR 3113 and PTR 3171 are novel selective analogs. Their amino acid positions, corresponding to the sequence of the native somatostatin SRIF-14, are described below.

PTR 3171 has a backbone to N terminus bridge connection.

The amino acid sequence of the corresponding backbone hexacyclic analogs is based on what are believed to be the most important amino acids derived from the native SRIF-14. From the data in the literature (SMS 210–995: A very potent and selective octapeptide analogue (i.e., Octreotide) of somatostatin having prolonged action, Bauer, et al. Life Sciences, Vol. 31, pp. 1133–1140, 1982), it was concluded that the amino acids of the native SRIF-14 in at least positions seven through 10, namely 7- Phe, 8- Trp, 9- Lys, and 10- Thr, and preferably positions six through 10, namely 6- Phe, 7- Phe, 8- Trp, 9- Lys, and 10- Thr, are essential to the pharmacophore of the hormone. The present innovative backbone analogs preferably include 5 to 8 amino acids, and are most preferably hexacyclic, with special amine acid modifications.

For the most preferred analogs, the amino acid Asn was substituted by the backbone Phe building unit at position 5. The configuration substitution of the native L-Trp at position 8 to D-Trp was made to improve the stability of the analog. The Thr residue at position 10 was deleted and the sequence completed by the corresponding backbone Phe building unit. The unique configuration substitution at position 9 from L-Lys to D-Lys as shown in PTRs 3123 and 3171 in comparison to PTR 3113 imparts improved selectivity of binding to the SST receptor subtype SSTR3 rather than SSTR5.

The present novel analogs provide an additional dimension to the novelty of the backbone cyclization technology, in the utilization of a shortened backbone bridge (i.e., only one to three methylenes beside the peptide bond). This approach enables one to obtain much greater rigidity of the peptide, and to further constrain the desired conformation of the native pharmacophore.

PTRs 3113, 3123, and 3171 preferably bind with higher affinity to a single receptor of the somatostatin receptor family, e.g., Somatostatin Receptor-3 (SSTR3). Previously studied analogs have failed to achieve specificity to this receptor subtype.

An additional advantage of the present analogs is related to their relative low molecular weight (their sequence consisting of only six amino acids), up to only 1000 daltons, in comparison to the most common somatostatin synthetic analogs which usually are hepta or octapeptides.

PTR 3123 and its analogs are as biostable as the conventional peptide Octreotide, and are much more stable than the native hormone SRIF-14, as tested in vitro against degradation of the most aggressive enzyme mixture in the body (e.g., renal homogenate) for up to 24 hours.

These peptide analogs induced physiological selectivity in vivo by inhibition of glucagon (related to glucagonoma, glucagonemia, hyperglycemia, NIDDM), but not on growth hormone ("GH") or insulin. PTRs 3113, 3123, and 3171 were found to be safe when administered intravenously to rats in a single dose of 6 mg/kg.

| 1 | 2 | 3 | 4 | 5 | 6 | 7 | 8 | 9 | 10 | 11 | 12 | 13 | 14 |
|---|---|---|---|---|---|---|---|---|---|---|---|---|---|
| Ala- | Gly- | Cys- | Lys- | Asn- | Phe- | Phe- | Trp- | Lys- | Thr- | Phe- | Thr- | Ser- | Cys |

| Position in SRIF: | 5 | 6 | 7 | 8 | 9 | 10 |
|---|---|---|---|---|---|---|
| PTR 3113 | Phe(C1)- | Phe- | Phe- | (D)Trp- | Lys- | Phe(N2)-NH2 |
| PTR 3123 | Phe(C1)- | Phe- | Phe- | (D)Trp- | (D)Lys- | Phe(N2)-NH2 |
| PTR 3171 | Phe*- | Phe- | Phe- | (D)Trp- | (D)Lys- | Phe(C2)-NH2 |

Another series of advantageous analogs are shown in the following table:
Position in SRIF:

|          | 5    | 6       | 7       | 8     | 9     | 10      | 11      | 12  |
|----------|------|---------|---------|-------|-------|---------|---------|-----|
| PTR 3205 |      | Phe*    | Phe     | D-Trp | Lys   | Thr     | Phe(C2) |     |
| PTR 3210 |      |         | Phe*    | D-Trp | Lys   | Thr     | Phe(C2) |     |
| PTR 3215 |      |         | Phe*    | D-Trp | D-Lys | Thr     | Phe(C2) |     |
| PTR 3220 |      |         | Ala(C1) | D-Trp | Lys   | Ala(N2) | Phe     |     |
| PTR 3225 |      |         | Ala(C1) | D-Trp | Lys   | Thr     | Phe(N2) |     |
| PTR 3230 |      |         | Ala(C1) | D-Trp | Lys   | Thr     | Ala(N2) |     |
| PTR 3235 |      | Ala(C1) | Phe     | D-Trp | Lys   | Thr     | Ala(N2) |     |
| PTR 3240 |      | Ala(C1) | Tyr     | D-Trp | Lys   | Val     | Phe(N2) |     |
| PTR 3245 |      | Ala*    | Phe     | D-Trp | D-Lys | Thr     | Ala(N2) |     |
| PTR 3250 | DPhe | Ala(C1) | Phe     | D-Trp | Lys   | Ala(N2) |         |     |
| PTR 3255 |      |         | Ala*    | D-Trp | Lys   | Thr     | Ala(C2) |     |
| PTR 3260 |      |         | Ala(S2) | D-Trp | Lys   | Thr     | Cys     |     |
| PTR 3265 |      |         | Ala(S2) | D-Trp | Lys   | Thr     | Cys     | Thr |
| PTR 3270 |      | Ala(S2) | Phe     | D-Trp | Lys   | Cys     |         |     |
| PTR 3275 |      | Ala(S2) | Phe     | D-Trp | Lys   | Thr     | Cys     | Thr |

The notation C2 denotes a building unit where the alkyl chain has two methylenes and the terminal (ω-functional) group is a carboxylic acid. The notation N2 designates a building unit where the alkyl chain is two methylenes and a terminal amino group. The designation S2 denotes a building unit where the alkyl chain has two methylenes and a terminal sulfhydryl group. The asterisk is used to designate where the building unit is attached. The Thr residues at position 12 in PTR 2265 and 2275 are preferably reduced to a terminal alcohol group. In general, the C terminal amino acid residue may include a carboxylic acid, an amide, an ester of may be reduced to a terminal alcohol group.

Preparation of Peptides with Backbone to Side Chain Cyclization

One preferred procedure for preparing the desired backbone cyclic peptides involves the stepwise synthesis of the linear peptides on a solid support and the backbone cyclization of the peptide either on the solid support or after removal from the support. The C-terminal amino acid is bound covalently to an insoluble polymeric support by a carboxylic acid ester or other linkages such as amides. An example of such support is a polystyrene-co-divinyl benzene resin. The polymeric supports used are those compatible with such chemistries as Fmoc and Boc and include for example PAM resin, HMP resin and chloromethylated resin. The resin bound amino acid is deprotected for example with TFA and to it is coupled the second amino acid, protected on the $N^\alpha$ for example by Fmoc, using a coupling reagent like BOP. The second amino acid is deprotected using for example piperidine 20% in DMF. The subsequent protected amino acids can then be coupled and deprotected at ambient temperature. After several cycles of coupling and deprotection that gives peptide, an amino acid having for example carboxy side chain is coupled to the desired peptide. One such amino acid is Fmoc-aspartic acid t-butyl ester. After deprotection of the $N^\alpha$ Fmoc protecting group, the peptide is again elongated by methods well known in the art. After deprotection a building unit for backbone cyclization is coupled to the peptide resin using for example the coupling reagent BOP. One such building unit is for example Fmoc-$N^\alpha$-(ω-Boc-amino alkylene)amino acid. After deprotection the peptide can then be elongated, to the desired length using methods well known in the art. The coupling of the protected amino acid subsequent to the building unit is performed by such coupling agents exemplified by PyBrOP to ensure high yield. After the linear, resin bound peptide, has been prepared the co-alkylene-protecting groups, for example Boc and t-Bu, are removed by mild acid such as TFA. The resin bound peptide is then divided into several parts. One part is subjected to n-resin cyclization using for example TBTU as cyclization gent in DMF to ensure high yield of cyclization, to give the backbone to side chain cyclic peptide resin. After cyclization on the resin the terminal amino protecting group is removed by agents such as piperidine and the backbone to side chain cyclic peptide is obtained after treatment with strong acid such as HF. Alternatively, prior to the removal of the backbone cyclic peptide from the resin, the terminal amino group is blocked by acylation with agents such as acetic anhydride, benzoic anhydride or any other acid such as adamantyl carboxylic acid activated by coupling agents such as BOP.

The other part of the peptide-resin undergoes protecting of the side chains used for cyclization, for example the ω-amino and carboxy groups. This is done by reacting the ω)-amino group with for example $Ac_2O$ and DMAP in DMF and activating the free ω-carboxy group by, for example, DIC and HOBT to give the active ester which is then reacted with, for example, $CH_3NH_2$ to give the non-cyclic analog of the cyclic peptide. Removal of the peptide from the resin and subsequent removal of the side chains protecting groups by strong acid such as HF to gives the non-cyclic analog of the backbone to side chain cyclic peptide.

The linear and/or non-cyclic analogs are used as reference compounds for the biological activity of their corresponding cyclic compounds.

Synthetic Approach for Generation of Backbone Cyclized Somatostatin Libraries

The general methodology for preparing the cyclic peptide libraries of this invention involves solid phase peptide synthesis using an orthogonal protection scheme which allows for chain elongation, selective removal of the protecting groups, cyclization of the protected peptides and removal of all side-chains protecting groups with or without cleavage from the resin. It is desirable that the various peptide sequences be present in the libraries in substantially equal amount.

The coupling reactions are performed by methods to create amide or ester bonds and are performed by methods familiar in the art as described herein. Typical coupling reagents are carbodiimides, activated anhydrides and esters and acyl halides. Reagents such as EDC, DCC, DPPA, PPA, BOP, PyBOP, PyBrop, HATU, HBTU, TBTU, HOBT and N-hydroxysuccinimide are typical.

After completion of the solid phase peptide elongation, by any scheme, portions of the peptide are cyclized via the bridging groups attached to the backbone amine bond nitrogens of the building units. It is preferable that a portion is retained in the non-cyclized form to serve as control during the biological or other screening assays. This portion of the peptide analog library, which contains the building units identical to those of the backbone cyclized library, but is devoid of the conformational constraint of the latter, is referred to as the "pre-cyclic". Alternatively, in any of the synthesis schemes, the backbone cyclization step may be performed and additional coupling cycles of amino acid residues may then be conducted.

Portions of the peptide may be cleaved from the resin and protecting groups removed, as required prior to assay of biological activity. The peptides are cleaved from the resin support by methods known in the art, the precise method being dependent upon the characteristics of the resin. It will be understood by those skilled in the art that the removal of certain protecting groups may occur simultaneously with cleavage of the peptide from the resin.

Typically the coupling between the resin and the first amino acid will form an ester bond, which will yield a carboxylic acid group on the peptide when it is cleaved from the resin. HMPB, Rink, PAM, Hycram and hydroxymethyl resins are exemplary. In addition, the carboxy terminal amino acid group may be converted to an amide, an ester or reduced to a terminal alcohol.

The reactive functional groups of the side chains of each amino acid or peptide are suitably protected as known in the peptide art. For example, the Boc, Cbz or Fmoc group may be used for protection of an amino group, especially an α-amino group. An alkyl (e.g., t-Bu, Me), chex, benzyl or allyl ester may be used for the protection of the side chain carboxyl of Asp or Glu. A benzyl, or suitably substituted benzyl, trityl, Alloc or T-Bu group is used to protect the mercapto group of cysteine, or other thiol containing residues; or the hydroxyl of Tyr, Ser or Thr. Cys and other sulfur-containing amino acids may also be protected by the Acm group or by formation of a disulfide with a thioalkyl (e.g., ethyl mercaptan) or thioaryl group. The benzyl/benzyloxymethyl, or a suitably substituted benzyl/benzyloxymethyl, Boc or formyl group may be used for protection of the imidazolyl group of His; and the Pmc, nitro, or a suitably substituted benzene-sulfonyl group (e.g., Ts, Mts) for protection of the guanidino nitrogen or Arg. The phthalamido, Boc, Fmoc, Alloc carbobenzyloxy or benzyl group, or suitably substituted benzyl or benzyloxy group, may be used for protecting the ε-amino group of lysine. Suitable substitution of the carbobenzyloxy or benzyl protecting groups is substitution with one to five chloro, bromo, nitro, methoxy or methyl groups, usually ortho and/or para, and is used to modify the reactivity of the protective group. These protective groups are removed by such methods as catalytic hydrogenation, sodium in liquid ammonia, hydrazine, base, TFA or HF treatment, as known in the art. The choice of side chain protecting groups is chosen so that they will not be removed under conditions which are used to deprotect the reactive functional group used in the coupling reaction (e.g., generally the a-amino group) to form the peptide backbone of the peptide chain. The protective group of the reactive functional group is removed prior to coupling each successive amino acid.

The bridging groups of the building units are used according to the present invention with an orthogonal protection scheme, such that these protecting groups can be removed selectively, under conditions which do not affect the protecting groups on the side chains or cleavage of the peptide from the resin. This enables backbone cyclization on the resin, which is preferred synthetically. Alternatively, the fully protected peptide may be removed from the resin, and cyclization performed in solution after selective removal of the protecting groups of the building units.

The cyclization reaction is carried out by means of selectively coupling the bridging group of one building unit to a bridging group of another building unit or amino acid side chain. By way of example, PyBOP is a particularly useful reagent for conducting the coupling reaction, in case of formation of an amide bond. To form a disulfide bridge oxidative conditions are used.

In a most preferred embodiment according to the present invention, the amino acid sequence scaffold is based on known active sequences from natural or synthetic peptides having somatostatin activity. It will thus be possible to further improve the activity of such known sequences upon rigidification of the active conformer.

Amino acids in certain positions are replaced by Backbone-Cyclization Building-Units or by natural and non-natural trifunctional amino acids such as Asp, Glu, Cys, Hcys, Lys, Orn and their D counterparts. Thus positional as well as structural scans are performed by changing the position of cyclization, the link of the ring to the backbone, the chirality at the position of cyclization, the ring forming bond, the ring size and the exact placement of the bond within the ring. These variations may also be performed in conjunction with changing the amino acid sequence of the peptide.

General synthesis of libraries of somatostatin analogs

To determine the optimum compounds for a particular application, a library of differently constrained analogs can be generated and then screened. The libraries can be synthesized on TentaGel amide Resin (substitution level of 0.2–0.3 mmol/g) using conventional solid-phase peptide synthesis known to those skilled in the art. NMP or DMF can be used as a solvent. A synthesis scale of 0.2–2 μmole for each peptide in library or sub-library is preferred, and all reactions can be performed at room temperature.

In each coupling step where more than one amino acid is to be coupled, the resin may be divided into the appropriate number of portions with a different amino acid added to each portion. Coupling is performed, twice for each position with 3 molar excess of each amino acid, 3 molar excess of PyBrop and 6 molar excess of DIEA for duration of 1–16 hours. All amino acids are protected with FMOC in their α-amine. Side-chain protections were as follow: His(Trt); Lys(Boc or Dde); Orn(Boc); Ser(tBu); Thr(tBu); Tyr(tBu).

After double coupling, the resin portions are washed, recombined and FMOC deprotection was performed using 20% piperidine in NMP for total of 20–40 minutes. After additional washes the resin can be divided again (if necessary) for the coupling of the next amino acid/s.

Before cyclization, the Allyl/Alloc protection of the amine and carboxyl of the building units is removed by treatment with a solution of 2 mole equivalents (one for each Allyl/Alloc molecule in peptide), of Pd(PPh3)$_4$ dissolved in chloroform containing 2.5% AcOH and 5% NMM for 2–2.5 hours or twice for 1 hour, resins are washed with the above solvent without the palladium before and after treatment, additional washes with NMP being made at the end of the removal process.

The peptides can be cleaved from the resin portions after washes with DCM, by double treatment with TFA 70%, H$_2$O 5%, TIS 1%, EDT 2.5%, DCM (mixture A) or TFA 70%, H$_2$O 5%, TIS 1%, Phenol 5%, DCM (mixture B) or 60%

TFA, 10% H₂O and 30% DCM (mixture C) plus additional wash with neat TFA. The three cleavage solutions of each resin portion are collected together, evaporated with nitrogen stream, 0.5–1 ml of H₂O is added to each sample that was then freeze-dried. The peptide mixtures are then partially purified on C-18 SEP-PAK (Millipore Corp.) using 0.1% acetic acid or TFA in H₂O as buffer A and 50–80% CH₃CN in 0.1% acetic acid/H₂O as buffer B and freeze-dried.

Each sub-library synthesized can be characterized by mass spectrometry (MALDI-TOF MS), and amino acid analysis.

General screening of somatostatin analogs

The resulting libraries are typically tested in vitro for their inhibition of the natural peptide (SRIF-14) binding to its 7-transmembranal receptors, and for their influence on second messengers and cell growth; and in vivo for inhibition of hormones and enzyme secretion.

The analogs can be further tested in vitro for their influence on cyclic adenosine monophosphate (cAMP) levels, tyrosine phosphatase activity, growth hormone secretion, and cell growth. The libraries can be further tested in vivo for the inhibition of growth-hormone release, and amylase, gastric acid, insulin and glucagon secretion in animals.

Metabolic stability tests as parameter for selection

Analogs are tested for stability by their resistance to enzymatic degradation by incubation in serum or in tissue homogenate, separation of the proteins and recording of the peptide peaks by HPLC before and after incubation. The peptide peaks that are not changed with increased incubation time are most stable. These peaks are separated and characterized by mass spectrometry, N-terminal sequence and comparison to purified peptide peaks. In this way the most stable peptides from library or sub-library are rapidly identified.

Conformationally constrained somatostatin analogs constructed based in part on the sequences of a number of known biologically active peptides or based on previously unknown novel sequences are presented in the examples below. The following examples are intended to illustrate how to make and use the compounds and methods of this invention and are in no way to be construed as a limitation.

EXAMPLES

Example 1

Resistance to biodegradation

The in vitro biostability of SST cyclic peptide analogs; PTRs 3113, 3123, and 3171, was measured in renal homogenate, and were compared to octreotide (Sandostatin™), and to native somatostatin (SRIF-14). The results are shown in the Table 1 below. In this assay, the backbone cyclic peptide analogs of the present invention were as stable as octreotide, and were much more stable than SRIF. The assay was based on HPLC determination of peptide degradation as a function of time in renal homogenate at 37° C.

TABLE 1

PERCENT OF INTACT MOLECULE AFTER INCUBATION IN RENAL HOMOGENATE

| Time (hours) | SRIF | Octreotide | PTR-3113 | PTR-3123 | PTR-3171 |
|---|---|---|---|---|---|
| 0 | 100 | 100 | 100 | 100 | 100 |
| 1 | 5 | 100 | 100 | 100 | 100 |
| 3 | 0 | 100 | 100 | 100 | 100 |
| 24 | 0 | 100 | 100 | 100 | 100 |

Example 2

Binding of somatostatin analogs

The somatostatin analogs were tested for their potency in inhibition of the binding of $^{125}I$-$Tyr^{11}$-SRIF (based on the method described by Raynor et. al., Molecular Pharmacology 43, 838–844, 1993) to membrane preparations expressing the transmembranal somatostatin receptors (SSTR-1,2, 3,4 or 5). The receptor preparations used for these tests were either from the cloned receptors selectively and stably expressed in Chinese Hamster Ovary (CHO) cells or from cell lines naturally expressing the SSTRs. Typically, cell membranes were homogenated in Tris buffer in the presence of protease inhibitors and incubated for 30–40 minutes with $^{125}I$-$Tyr^{11}$-SRIF with different concentrations of the tested sample. The binding reactions were filtered, the filters were washed and the bound radioactivity was counted in gamma counter. Non specific binding was defined as the radioactivity remaining bound in the presence of 1 μM unlabeled SRIF-14.

In order to validate positive signals of the binding tests, and to eliminate non-specific signals, samples of irrelevant peptides, such as GnRH, that were synthesized and handled using the same procedures, were tested in the same assays as negative control samples. These samples had no binding activity in any of the assays. Results are shown below in Table 2.

TABLE 2

PERCENT INHIBITION OF SRIF-14 BINDING OF PTRS TO CLONED HUMAN SOMATOSTATIN RECEPTORS

| | SST-R3 | | | SST-R5 | | |
|---|---|---|---|---|---|---|
| Concentration | $10^{-8}M$ | $10^{-7}M$ | $10^{-6}M$ | $10^{-8}M$ | $10^{-7}M$ | $10^{-6}M$ |
| PTR-3113 | 16 | 65 | 94 | 0 | 50 | 86 |
| PTR-3123 | 24 | 41 | 84 | 0 | 0 | 0 |
| PTR-3171 | 12 | 40 | 87 | 18 | 10 | 60 |
| Total counts | | 12000 CPM | | | 3600 CPM | |
| Non-specific binding | | 1200 CPM | | | 900 CPM | |
| blank | | 400 CPM | | | 400 CPM | |

Example 4

The effect of somatostatin analogs on the release of growth hormone

In vivo determination of the pharmacodynamic properties of cyclic peptide somatostatin analogs was carried out in rats, according to known procedures. Inhibition of Growth Hormone (GH) release as a result of peptide administration was measured in Wistar male rats. The analog activity was compared in this study to SRIF or to octreotide using 4 rats in each group. Time course profiles for GH release under constant experimental conditions were measured.

Methods

Adult male Wistar rats weighing 200–350 g, were maintained on a constant light-dark cycle (light from 8:00 to 20:00 h), temperature (21±3° C.), and relative humidity (55±10%). Laboratory chow and tap water were available ad libitum. On the day of the experiment, rats were anesthetized with Nembutal (IP, 60 mg/kg). Ten minutes after anesthesia, drugs were administered S.C. at 100 microgram/kg dose. Sampling was carried out at 30 minutes after peptide administration. Blood samples were collected by jugular vein cannulation into tubes containing heparin (15 units per ml of blood) and centrifuged immediately. Plasma was separated and kept frozen at &31 20° C. until assayed.

Rat growth hormone (rGH) [$^{125}$I] levels were determined by means of a radioimmunoassay kit (Amersham). The standard in this kit has been calibrated against a reference standard preparation (NIH-RP2) obtained from the National Institute of Diabetes and Digestive and Kidney Diseases. All samples were measured in duplicate. The results of these experiments are shown below in Table 3 and in FIG. 1.

TABLE 3

PLASMA GROWTH HORMONE CONCENTRATION (ng/ml)

| | Control | None | Octreotide | PTR-3123 |
|---|---|---|---|---|
| | 1.03 | | 0.48 | 10 |
| | 10 | 0.46 | 0.56 | 6.37 |
| | 10 | 2.7 | 0.46 | 7.4 |
| | 10 | 4.54 | 0.43 | 10 |
| | 10 | | 0.43 | 10 |
| | 10 | | 0.61 | 10 |
| Average | 8.72 | 2.33 | 0.50 | 8.96 |
| SE | 1.28 | 0.87 | 0.03 | 0.67 |

Example 5

The effect of somatostatin analogs on the release of glucagon

In vivo determination of the release of glucagon as a result of peptide administration was measured in Wistar male rats. The analog activity was compared in this study to SRIF or to Octreotide using 4 rats in each group. Time course profiles for glucagon release under constant experimental conditions were measured.

Figure 2:
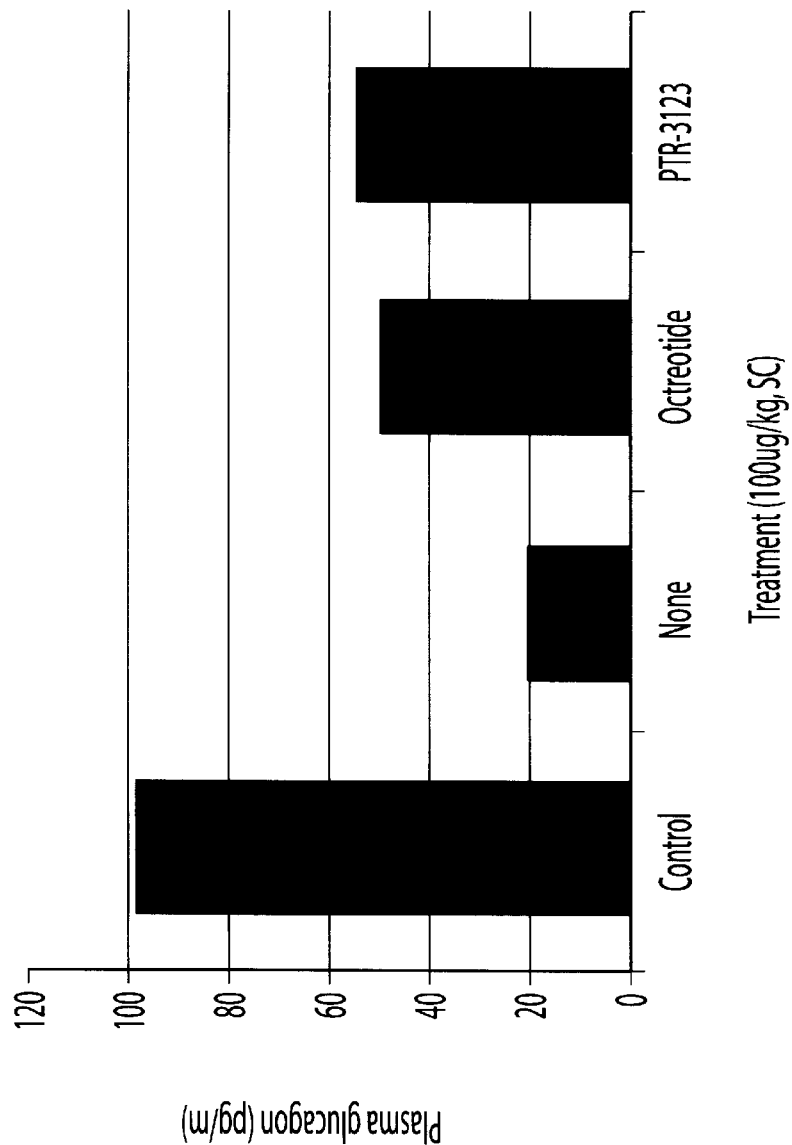
FIG. 2 is a graph showing the effect of somatostatin analogs on the release of glucagon compared to octreotide.

Male Wistar rats were fasted overnight. Animals were anesthetized with Nmbutal (IP, 60 mg/kg). Ten minutes after anesthesia, drugs were administrated S.C. at 100 microgram/kg dose. Stimulation of glucagon secretion was performed by I.V. administration of L-Arginine, 0.6 g/kg, 5 minutes before blood collection from portal vein. Hormone concentration was measured by RIA. Results are shown below in Table 4 and FIG. 2.

TABLE 4

PLASMA GLUCAGON CONCENTRATION (ng/ml)

| | Control | None | Octreotide | PTR-3123 |
|---|---|---|---|---|
| | 189 | 18 | 20 | 58 |
| | 76 | 9.5 | 89 | 52 |
| | 145 | 32 | 62 | 20 |
| | 37 | 20 | 70 | 84 |
| | 131 | | 37 | 87 |

TABLE 4-continued

PLASMA GLUCAGON CONCENTRATION (ng/ml)

| | Control | None | Octreotide | PTR-3123 |
|---|---|---|---|---|
| | 44 | | 20 | 20 |
| | 67 | | | |
| Average | 98.4 | 19.9 | 49.7 | 53.5 |
| SE | 21.6 | 4.6 | 11.6 | 12.0 |

Example 6

The effect of somatostatin analogs on insulin release.

An in vivo determination of insulin release as a result of peptide administration was measured in Wistar male rats. The analog activity was compared in this study to SRIF or to octreotide using 4 rats in each group. Time course profiles for GH release under constant experimental conditions were measured.

Figure 3:
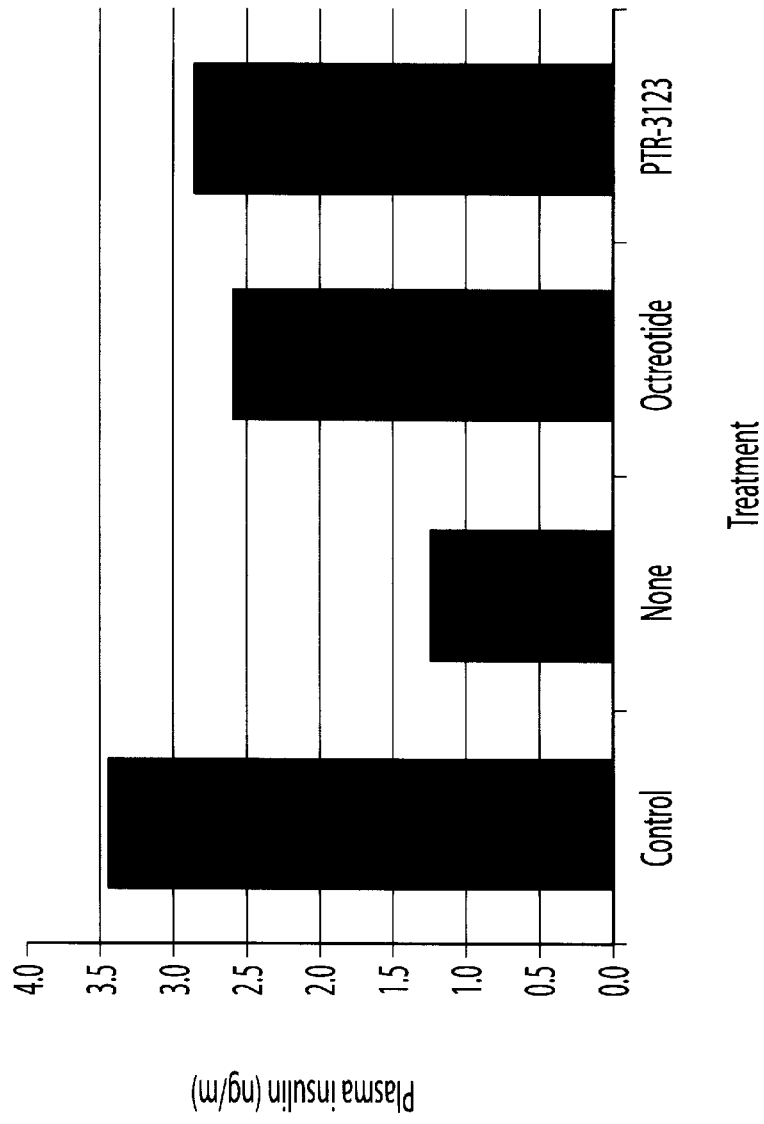
FIG. 3 is a graph showing the effect of somatostatin analogs on the release of insulin compared to octreotide.

Male Wistar rats were fasted overnight. Animals were anesthetized with Nembutal (IP, 60 mg/kg). Ten minutes after anesthesia, drugs were administrated S.C. at 100 microgram/kg dose. Stimulation of glucagon secretion was performed by I.V. administration of L-Arginine, 0.6 g/kg, and 5 minutes before blood collection from abdominal Vena-cava. Hormone concentration was measured by RIA. Results are shown below in Table 5 and in FIG. 3.

TABLE 5

PLASMA INSULIN CONCENTRATION (ng/ml)

| | Control | None | Octreotide | PTR-3123 |
|---|---|---|---|---|
| | 3.97 | 1 | 3.5 | 1.46 |
| | 4.14 | 2.5 | 1.95 | 5.66 |
| | 5.12 | 0.7 | 3.7 | |
| | 3.8 | 0.74 | 3.06 | 2.44 |
| | 2.7 | | 2 | 1.87 |
| | 3 | | 1.1 | 2.8 |
| | 1.5 | | | |
| Average | 3.46 | 1.24 | 2.55 | 2.85 |
| SE | 0.44 | 0.43 | 0.42 | 0.74 |

None = no stimulation with L-Arginine
Control = vehicle

What is claimed is:

1. A backbone cyclized somatostatin analog comprising a peptide sequence of four to twelve amino acids that incorporates at least two building units, each of which contains one nitrogen atom of the peptide backbone connected to a bridging group comprising an amide, thioether, thioester or disulfide, wherein the at least two building units are connected to the bridging group to form a cyclic structure.

2. The backbone cyclized somatostatin analog of claim 1 wherein the peptide sequence incorporates five to eight amino acids.

3. The backbone cyclized somatostatin analog of claim 1 having the general formula

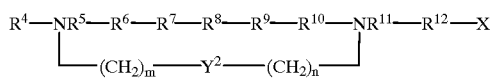

wherein m and n are 1 to 5;

X designates a terminal carboxy acid, amide or alcohol group;

$R^4$ is absent or is a terminal group of one to four amino acids;

$R^5$ is Nal, β-Asp (Ind), Gly, Tyr, (D)- or (L)-Ala, or (D)- or (L)-Phe;

$R^6$ and $R^7$ may be absent, or are independently Gly, Tyr, (D)- or (L)-Ala, or (D)- or (L)-Phe;

$R^8$ is (D)- or (L)-Trp;

$R^9$ is (D)- or (L)-Lys;

$R^{10}$ is absent or is Gly, Abu, Cys, Thr, Val, (D)- or (L)-Ala, or (D)- or (L)-Phe;

$R^{11}$ is Cys, (D)- or (L)-Ala, or (D)- or (L)-Phe;

$R^{12}$ is absent or is Val, Thr, or Nal; and $Y^2$ is amide, thioether, thioester or disulfide.

4. The backbone cyclized somatostatin analog of claim 3 wherein m and n are each 1, 2 or 3.

5. The backbone cyclized somatostatin analog of claim 3 wherein:

$R^4$ is absent;

$R^5$ is (D)- or (L)-Phe, or (D)- or (L)-Ala;

$R^6$ may be absent and $R^6$, when present, and $R^7$ are independently (D)- or (L)-Phe, Ala or Tyr;

$R^{10}$ is absent or is Thr, Val or (D)- or (L)-Phe;

$R^{11}$ is (D)- or (L)-Ala, or (D)- or (L)-Phe; and $R^{12}$ is absent.

6. The backbone cyclized somatostatin analog of claim 3 wherein:

$R^5$ is (D)- or (L)-Ala, or (D)- or (L)-Phe;

$R^6$ is absent or is (D)- or (L)-Ala, or (D)- or (L)-Phe;

$R^7$ is (D)- or (L)-Ala, or (D)- or (L)-Phe;

$R^{10}$ is absent or is Thr, Cys, (D)- or (L)- Ala;

$R^{11}$ is Cys, (D)- or (L)-Ala, or (D)- or (L)-Phe; and $R^{12}$ is absent or is Thr.

7. The backbone cyclized somatostatin analog of claim 1 having the general formula:

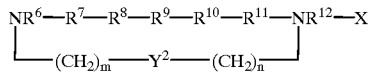

wherein m and n are 1 to 5

$R^6$ is (D)- or (L)-Ala, or (D)- or (L)-Phe;

$R^7$ is absent or is Tyr, (D)- or (L)- Ala, or (D)- or (L)- Phe;

$R^{10}$ is Thr, Val, Cys or (D)- or (L)-Ala;

$R^{11}$ is Cys, (D)- or (L)-Ala, or (D) or (L)-Phe;

$R^{12}$ is Thr; and $Y^2$ is amide, thioether, thioester or disulfide.

8. The backbone cyclized somatostatin analog of claim 7, wherein:

$R^6$ is (D)- or (L)-Ala;

$R^7$ is absent or is (D)- or (L)-Phe;

$R^{10}$ is Thr;

$R^{11}$ is Cys; and

X is an alcohol group.

9. The backbone cyclized somatostatin analog of claim 1 having the general formula

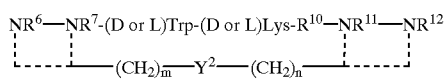

wherein the dotted line indicates that the bridge is connected to $NR^6$ or $NR^7$ at one end and to $NR^{11}$ or $NR^{12}$ at the other end;

$R^6$ is absent or is (D)- or (L)-Phe or Ala;

$R^7$ is (D)- or (L)-Phe, Ala or Tyr;

$R^8$ is Thr, Ala, Val or Cys;

$R^{11}$ is absent or is (D)- or (L)-Phe, Ala or Cys;

$R^{12}$ is absent or is Thr or Thr reduced to an alcohol; and $Y^2$ is amide, thioether, thioester or amide.

10. The backbone cyclized somatostatin analog of claim 9 wherein the bridge is connected to $NR^6$ and $NR^{11}$ or to $NR^6$ and $NR^{12}$ with $R^{12}$ being Thr reduced to an alcohol.

11. The backbone cyclized somatostatin analog of claim 1 having one of the following formulae:

NPhe - Phe - D-Trp - Lys - Thr - NPhe - X

NPhe - D-Trp - Lys - Thr - NPhe - X

NPhe - D-Trp - D-Lys - Thr - NPhe - X

NAla - D-Trp - Lys - Ala - NPhe - X

NAla - D-Trp - Lys - Thr - NPhe - X

NAla - D-Trp - Lys - Thr - NAla - X

NAla - Phe - D-Trp - Lys - Thr - NAla - X

NAla - Tyr - D-Trp - Lys - Val - NPhe - X

NAla - Phe - D-Trp - D-Lys - Thr - NAla - X

ND-Phe - Ala - Phe - D-Trp - Lys - NAla - X

NAla - D-Trp - Lys - Thr - NAla - X

NAla - D-Trp - Lys - Thr - NCys - X

NAla - D-Trp - Lys - Thr - Cys - NThr - X

NAla - Phe - D-Trp - NLys - Cys - X

NAla - Phe - D-Trp - Lys - Thr - Cys - NThr - X

NPhe - Phe - Phe - D-Trp - Lys - NPhe - X

NPhe - Phe - Phe - D-Trp - D-Lys - NPhe - X or

NPhe - Phe - Phe - D-Trp - D-Lys - NPhe - X where X is -NH2 or -OH and the bridging group extends between the amino acids that are preceded by the letter N.

12. A pharmaceutical compound comprising one of the backbone cyclized somatostatin analogs of claim 1 and a pharmaceutically acceptable carrier.

13. A pharmaceutical compound comprising one of the backbone cyclized somatostatin analogs of claim 7 and a pharmaceutically acceptable carrier.

14. A pharmaceutical compound comprising one of the backbone cyclized somatostatin analogs of claim 9 and a pharmaceutically acceptable carrier.

15. A pharmaceutical compound comprising one of the backbone cyclized somatostatin analogs of claim 11 and a pharmaceutically acceptable carrier.

* * * * *

UNITED STATES PATENT AND TRADEMARK OFFICE
CERTIFICATE OF CORRECTION

PATENT NO.   :   6,051,554

DATED        :   April 18, 2000

INVENTORS    :   Verek Hornik et al.

It is certified that error appears in the above-identified patent and that said Letters Patent is hereby corrected as shown below:

On the Face Page, under the heading Related U.S. Application Data, please delete "application no. 08/690,609, Patent No. 5,748,643" and insert:
-- application no. 08/690,090, Patent No. 5,770,687--.

Signed and Sealed this

Eighth Day of May, 2001

*Attest:*

NICHOLAS P. GODICI

*Attesting Officer*   Acting Director of the United States Patent and Trademark Office